(12) United States Patent
Mabini et al.

(10) Patent No.: US 12,290,463 B2
(45) Date of Patent: May 6, 2025

(54) MECHANISM FOR AUTOMATED INJURY STABILIZATION AND TREATMENT

(71) Applicant: Secured Injury Devices, Inc., San Diego, CA (US)

(72) Inventors: Jerry Mario Mabini, San Diego, CA (US); Alex Balazs, San Diego, CA (US); Julian Banfield, Melbourne (AU)

(73) Assignee: Secured Injury Devices, Inc., San Diego, CA (US)

( * ) Notice: Subject to any disclaimer, the term of this patent is extended or adjusted under 35 U.S.C. 154(b) by 424 days.

(21) Appl. No.: 17/665,555

(22) Filed: Feb. 6, 2022

(65) Prior Publication Data

US 2022/0168130 A1   Jun. 2, 2022

Related U.S. Application Data

(63) Continuation-in-part of application No. 17/394,970, filed on Aug. 5, 2021.

(60) Provisional application No. 63/063,143, filed on Aug. 7, 2020.

(51) Int. Cl.
*A61F 5/058* (2006.01)
*A61F 7/02* (2006.01)
*A61F 7/03* (2006.01)

(52) U.S. Cl.
CPC ............ *A61F 5/05816* (2013.01); *A61F 7/03* (2013.01); *A61F 2007/0233* (2013.01)

(58) Field of Classification Search
CPC .... A61F 5/012; A61F 5/0127; A61F 5/05816; A61F 5/0585; A61F 7/03; A61F 2007/0044; A61F 2007/0091; A61F 2007/0233; A61F 2007/0268
See application file for complete search history.

(56) References Cited

U.S. PATENT DOCUMENTS

| | | | |
|---|---|---|---|
| 2,329,590 | A | 9/1943 | Charney |
| 3,039,061 | A | 6/1962 | Dome |
| 3,080,986 | A | 3/1963 | Eriekson |
| 5,395,399 | A | 3/1995 | Rosenwald |

(Continued)

FOREIGN PATENT DOCUMENTS

| | | |
|---|---|---|
| CN | 204219137 | 3/2015 |
| CN | 110974527 | 4/2020 |

(Continued)

OTHER PUBLICATIONS

What is a Valve, Garlock, Aug. 18, 2015.*

(Continued)

*Primary Examiner* — Alireza Nia
*Assistant Examiner* — Andrew Jun-Wai Mok
(74) *Attorney, Agent, or Firm* — MLO, a professional corp.

(57) ABSTRACT

Systems and methods are disclosed that relate to a stabilization and cooling apparatus having a stabilizing structure with at least one inflatable chamber, the stabilizing structure configured to become semi-rigid upon inflation of the at least one inflatable chamber. A cooling structure is integrated with the stabilizing structure and includes a single-use cooling element and a thermally conductive material in thermal communication with the single-use cooling element. The apparatus also has an actuator configured to cause inflation of at least one inflatable chamber.

15 Claims, 12 Drawing Sheets

(56) References Cited

U.S. PATENT DOCUMENTS

| | | | |
|---|---|---|---|
| 5,407,421 | A | 4/1995 | Goldsmith |
| 6,099,555 | A | 8/2000 | Sabin |
| 6,602,213 | B1 | 8/2003 | Figley |
| 7,063,676 | B2 | 6/2006 | Barak |
| 10,492,940 | B2 | 12/2019 | Ingimundarson |
| 10,675,166 | B2 | 6/2020 | Paulos |
| 10,751,221 | B2 | 8/2020 | Avitable |
| 10,813,825 | B2 | 10/2020 | Schubert |
| 10,842,659 | B2 | 11/2020 | Best |
| 10,932,939 | B1 | 3/2021 | Pahls |
| 10,952,886 | B2 | 3/2021 | Thorsteinsdottir |
| 11,166,869 | B2 | 11/2021 | Gensch |
| 11,179,260 | B2 | 11/2021 | Best |
| 11,246,728 | B2 | 2/2022 | Danek |
| 11,253,384 | B2 | 2/2022 | Petursson |
| 11,376,147 | B2 | 7/2022 | Stefansson |
| 11,412,788 | B2 | 8/2022 | Teixeira Rangel |
| 11,517,462 | B2 | 12/2022 | Gildersleeve |
| 2002/0103520 | A1 | 8/2002 | Wade |
| 2007/0161932 | A1 | 7/2007 | Pick |
| 2008/0147153 | A1 | 6/2008 | Quincy |
| 2010/0125317 | A1 | 5/2010 | Lu |
| 2013/0072838 | A1 | 3/2013 | Fischer |
| 2014/0193407 | A1 | 7/2014 | Herring |
| 2015/0297397 | A1* | 10/2015 | Rand .............. A61F 7/02 607/110 |
| 2016/0354222 | A1* | 12/2016 | Alsolami .............. E02F 3/964 |
| 2017/0209306 | A1 | 7/2017 | Rand |
| 2018/0001499 | A1 | 1/2018 | Stojanovski |
| 2018/0014995 | A1* | 1/2018 | Gensch .............. A61H 9/0085 |
| 2020/0014688 | A1 | 1/2020 | Kohli |
| 2020/0015937 | A1 | 1/2020 | Stewart |
| 2020/0214869 | A1 | 7/2020 | Popov |
| 2020/0268592 | A1 | 8/2020 | Johnson |
| 2020/0360223 | A1 | 11/2020 | Park |
| 2020/0375283 | A1 | 12/2020 | Check |
| 2020/0405533 | A1 | 12/2020 | Check |
| 2021/0085519 | A1* | 3/2021 | Rand .............. A61F 7/106 |
| 2021/0260399 | A1 | 8/2021 | Kariguddaiah |
| 2022/0000650 | A1 | 1/2022 | Kim |
| 2022/0039996 | A1 | 2/2022 | Mabini |

FOREIGN PATENT DOCUMENTS

| | | |
|---|---|---|
| CN | 111053538 | 4/2020 |
| CN | 111053638 | 4/2020 |
| CN | 115368877 | 11/2022 |
| EP | 3797741 | 3/2021 |
| FR | 3032112 | 8/2016 |
| FR | 3039061 | 1/2017 |
| FR | 3080986 | 11/2019 |
| GB | 2329590 | 3/1999 |
| WO | 2014193407 | 12/2014 |

OTHER PUBLICATIONS

What is a Valve, Garlock, Aug. 18, 2015 (Year: 2015).*

International Search Report and Written Opinion, International Application No. PCT/US2021/044844, International Filing Date Aug. 5, 2021, mailed Nov. 22, 2021.

Diana N. Pei, PharmD, "What's Inside an Ice Pack?" Poison Control, National Capital Poison Center, https://www.poison.org/articles/whats-inside-ice-packs-20 (3 pages).

Emanuele Mortarotti, "What's inside an ice pack?" Dispotech, Jan. 5, 2022, https://www.dispotech.com/en/blog/what-s-inside-an-ice-pack (9 pages).

"Inflatable Back Brace," Wishing Well Medical, Medical Equipment Sales & Rentals, https://www.wishingwellmedical.com/product/inflatable-back-brace (3 pages).

OrthoBrace™, Orthopaedic Bracing and Supports, Catalogue 2021-2022, https://d347awuzx0kdse.cloudfront.net/orthobrace/content-file/OrthoBrace%20A4%20Catalogue%202021-22%20LR-compressed.pdf?v=7286115be7f0cd2b58a11e0a9134a510c2930214 (72 pages).

Bauerfeind®, Product Catalog: Supports and Orthoses, 2022, https://www.bauerfeind-group.com/fileadmin/user_upload/bf-germany_bf-international/_downloads/produktkatalog-orthopaedie-EN-INT.pdf (132 pages).

Jaspo Secure Hybrid Wrist Safety Protection Guards—Pink (Small), https://www.jasposports.com/gloves-wrist-guard/jaspo-secure-hybrid-wrist-safety-protection-guards-pink-small (2 pages).

Air-Stirrup Ankle Fracture Support Ankle Brace (Size—Universal), Meesho, https://www.meesho.com/airstirrup-ankle-fracture-support-ankle-brace-size-universal/p/140hp5 (13 pages).

Orthopaedics, Yumpu, https://www.yumpu.com/en/document/read/26464994/orthopaedics (Slide 1 of 128).

Aircast Devices, Chitarath, https://www.indiamart.com/chitrarath/aircast-devices.html (8 pages).

Pro Lite Low Profile Wrist Splint 6, Westmont Pharmacy, https://shop.westmontpharmacy.com/pro-lite-low-profile-wrist-splint-6/ (Web page defunct—see archived page: https://web.archive.org/web/20230130012939/https://shop.westmontpharmacy.com/pro-lite-low-profile-wrist-splint-6/ ) (3 pages).

Tynor Knee Wrap Neoprene, Grey, 1 Unit, Tynor, https://www.tynorstore.com/product/knee-wrap-neoprene (3 pages).

Tynor Wrist Splint Ambidextrous, Grey, 1 Unit, Tynor, https://www.tynorstore.com/product/wrist-splint-ambidextros (3 pages).

Tynor D-11 Knee Immobilizer 19 Large, TATA 1mg, https://www.1mg.com/otc/tynor-d-11-knee-immobilizer-19-large-btc345608 (7 pages).

Tynor Wrist Splint (Ambidextrous) (E 43), Skytech Medical & Surgical Devices, https://surgicalshoppe.co.in/product/tynor-wrist-splint-ambidextrous-I-e-43 (6 pages).

Michael Hinckley, "What Chemicals Are Used in Instant Ice Packs?"; Mar. 13, 2018; <https://sciencing.com/chemicals-sued-instant-ice-packs-5405231.html> (Year: 2018).

* cited by examiner

US 12,290,463 B2

MECHANISM FOR AUTOMATED INJURY STABILIZATION AND TREATMENT

RELATED APPLICATION(S)

This application is a continuation-in-part of U.S. patent application Ser. No. 17/394,970, filed Aug. 5, 2021, titled "Mechanism for Automated Injury Stabilization and Treatment," that claims priority to and the benefit of U.S. Provisional Application No. 63/063,143, filed Aug. 7, 2020, titled "Mechanism for Automated Injury Stabilization and Treatment," the disclosures of each are hereby incorporated by reference.

DESCRIPTION OF THE RELATED ART

In response to common injuries such as sprained or torn tendons or ligaments, dislocated joints, or broken bones, treatments can include immobilizing the affected area and/or applying a thermal treatment (heat/cold) to reduce pain or swelling. For example, an ice pack is often applied at the time of injury. In some cases, devices are also used to immobilize the injured region to prevent further injury.

SUMMARY

A stabilization and cooling apparatus is disclosed that has a stabilizing structure with at least one inflatable chamber, where the stabilizing structure is configured to become semi-rigid upon inflation of the at least one inflatable chamber. A cooling structure is integrated with the stabilizing structure and includes a single-use cooling element and a thermally conductive material in thermal communication with the single-use cooling element. The stabilization and cooling apparatus also includes an actuator configured to cause inflation of the at least one inflatable chamber.

In some variations, the stabilizing structure can be further configured to approximate an anatomical shape upon inflation, such as a wrist, shoulder, hip, knee, or ankle. The stabilizing structure can include a plurality of inflatable chambers.

In other variations, the single-use cooling element can be configured to cause an endothermic reaction, for example, with the single-use cooling element including water and ammonium chloride. In some variations, there can be a second actuator configured to cause mixing of the ammonium chloride and water to generate the endothermic reaction.

In some variations, the apparatus can be further configured to initiate cooling without the need to stir or shake the apparatus, and may be further configured to initiate cooling through removal of a separator located between containers holding water and sodium chloride.

In yet other variations, there can be a thermally conductive material on a portion of the cooling structure facing a patient and the cooling structure can further include a thermally insulating material between the cooling structure and the stabilizing structure.

In some variations, the actuator can be further configured to also initiate cooling by the cooling element. A single mechanical component can be configured to activate a pressured gas source and also break or remove a removable separator to permit reactants in the cooling structure to mix and cool.

In other variations, an actuator can be further configured to open a pressurized gas source. A container can hold a reactant and opening a pressurized gas source causes the reactant to be directed from the container to the single-use cooling element through a first valve.

In some variations, gas from the pressurized gas source causes inflation of an inflatable chamber through a second valve, following the reactant being directed to the single-use cooling element through the first valve.

In an interrelated aspect, a method is disclosed that includes applying, to an injured portion of a patient, an apparatus in accordance with any of the features disclosed herein and activating the actuator to cause inflation of the at least one inflatable chamber in order to stabilize the injured portion and also to cause cooling in order to cool the injured portion.

In another aspect, an apparatus can include a housing having a gas input port, a gas output port, a first input port, a first output port, a second input port, and a second output port; an actuator configured to open a pressurized gas source coupled to the gas input port; a first valve configured to direct a reactant from the first input port to the first output port; and a second valve configured to direct gas from the second input port to the second output port.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Previous approaches to injury treatment rely on multiple apparatuses, often utilizing multiple steps to achieve patient stabilization and thermal treatment (e.g., applying cold therapy to reduce swelling). The present disclosure provides systems and methods for substantially simultaneous immobilization and thermal treatment. Such implementations advantageously reduce the amount of time between injury and treatment. This reduction can be critical for medical personnel attempting to diagnose the injury as allowing movement or allowing excessive swelling can obscure the actual injury, cause further injury, or both.

Figure 1:
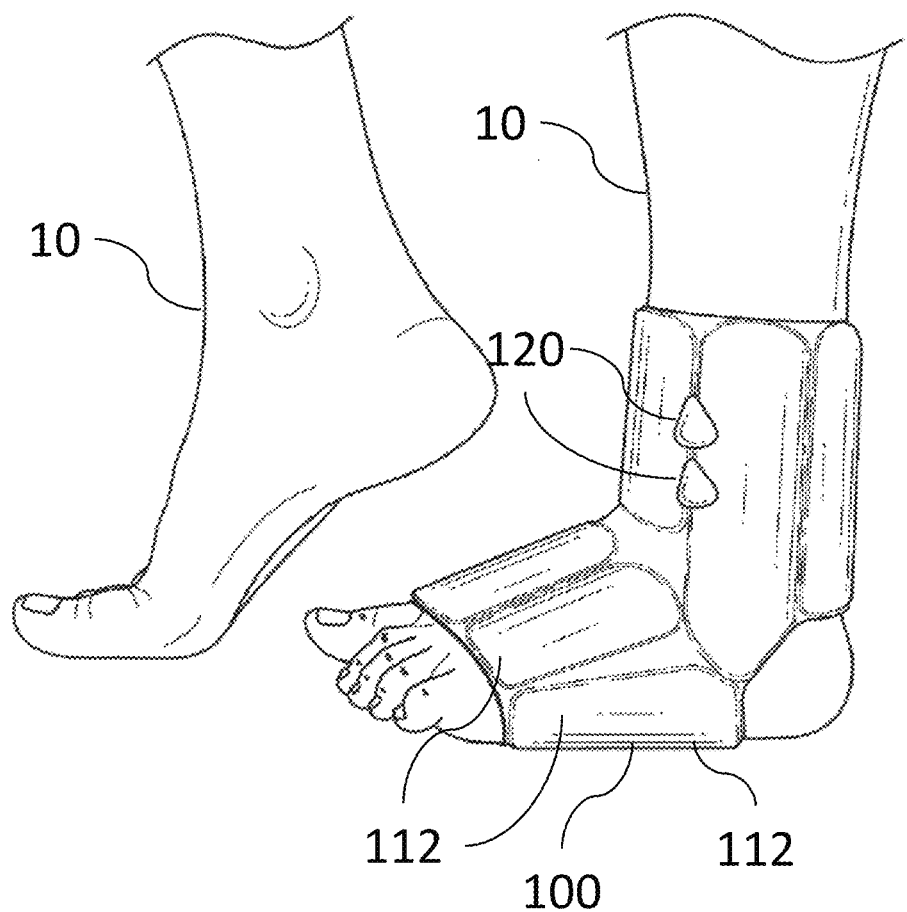
FIG. 1 is a simplified diagram illustrating a patient's ankle immobilized with a stabilization and cooling apparatus in accordance with certain aspects of the present disclosure.

FIG. 1 illustrates one example of an apparatus 100 that can provide both stabilization and cooling for a patient 10. An injured ankle is depicted in the left portion of FIG. 1 showing the ankle in a position that may not be ideal from a medical perspective. In the right portion of FIG. 1, an implementation of the disclosed stabilization and cooling apparatus 100 has been applied to the injured ankle of patient 10. As shown, the stabilization and cooling apparatus (also referred herein to as the "apparatus") has stabilized the patient's ankle in a proper position.

Apparatus 10 is depicted with a stabilizing structure 110 formed of several inflatable chambers 112 that provide compression to immobilize the injured location. As described further herein, apparatus 100 can also include a cooling structure to provide rapid cooling of the injured location. Such stabilization and cooling can be initiated by a user via one or more actuators 120 (e.g., pull tabs) that cause the substantially simultaneous stabilization and/or cooling.

Figure 2:
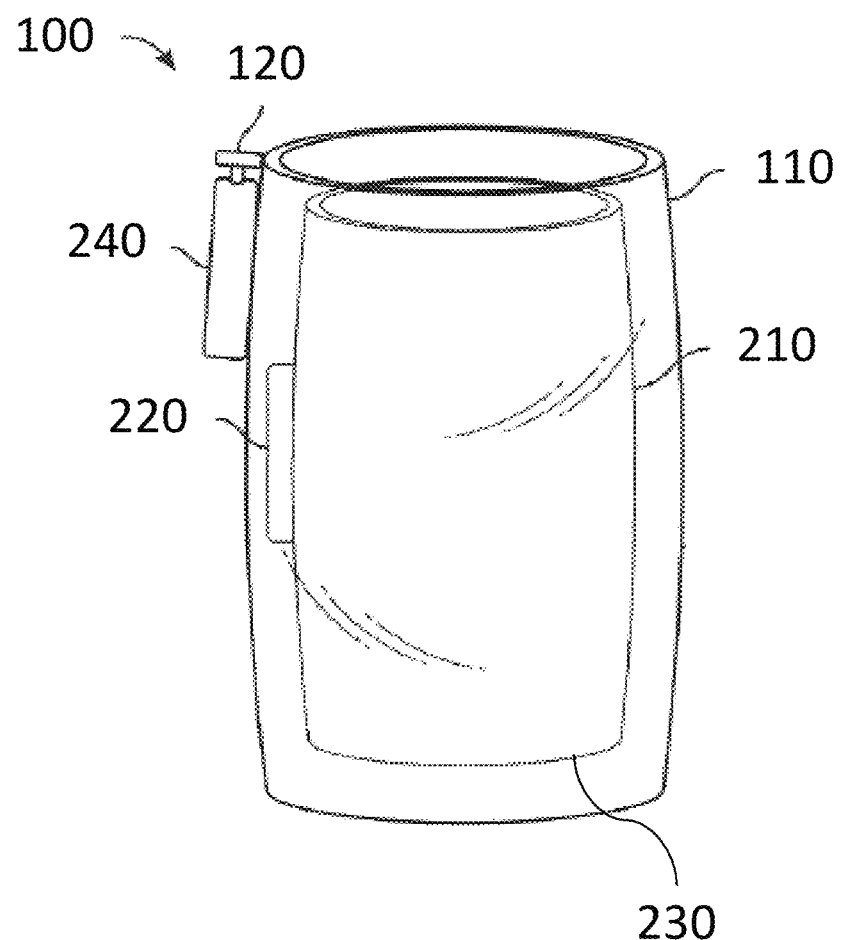
FIG. 2 is a simplified diagram illustrating an exemplary stabilizing structure and cooling structure in accordance with certain aspects of the present disclosure.

FIG. 2 conceptually illustrates certain features of the disclosed apparatuses. As shown, implementations of the disclosed stabilization and cooling apparatus 100 can have two primary components. First, there can be a stabilizing structure 110 including one or more inflatable chambers 112 (e.g., as shown in FIG. 1, with FIG. 2 depicting a more generalized illustration), with the stabilizing structure 110 configured to become semi-rigid upon inflation of the inflatable chamber(s) 112. For example, the rigidity of the inflated stabilizing structure 110 can prevent substantial movement of the injured portion of the patient, thus preventing further injury as described above. As used herein, "semi-rigid" means that the flexibility of the stabilizing structure is reduced so that it retains a shape approximating an enclosure of the injured portion of the patient. Implementations of the semi-rigid stabilizing structure can have different shapes, for example, an elbow-shaped apparatus can have a semi-rigid shape that secures the patient's elbow in an extended (i.e., straight) shape, a partially bent shape (e.g., 45 or 90 degrees), or a full bent shape (as much as allowable by the patient's anatomy).

Second, there can also be a cooling structure 210 integrated with the stabilizing structure. This integration can provide therapeutic and manufacturing advantages not available in prior art devices such as those that require external sources of cooling such as adding ice packs, etc. As used herein, the term "integration" means that the stabilizing structure and cooling structure form a single apparatus by design, rather than being a combination of devices that are intended to be used separately (e.g., an immobilization mechanism and a separate cooling mechanism that must be added by a user). Furthermore, implementations described herein May describe a cooling structure disposed inside the stabilizing structure. As used herein, "[the cooling structure] inside [the stabilizing structure]" means some portions of the cooling structure are closer to the patient than the stabilizing structure (typically a substantial portion). This is depicted, for example, in FIG. 2. Further, other implementations can include the cooling structure being surrounded by or layered between stabilizing structures. In general, it is contemplated that the integrated nature of the apparatus, in any embodiments herein, allows for any relative disposition and layers of stabilizing structure 110 and cooling structure 210.

As depicted in FIG. 2, some implementations can include a single-use cooling element 220 and a thermally conductive material 230 in thermal communication with the single-use cooling element 220. A thermally conductive material can be, e.g., a material having a fairly large thermal conductivity as compared to air or insulating materials such as plastic or certain foams. The placement of thermally conductive material in, as part of, or adjacent the cooling structure can direct the cooling to desired locations at or around the injury location.

Also illustrated in FIG. 2, is an exemplary actuator 120. Apparatuses, as discussed herein, may include one or more actuators to effect, for example, cooling and/or inflation. These actuators may take any typical form and may include, for example, one or more of a button, a switch, a pull tab, a ring, a cord, etc. In one exemplary embodiment, actuator 120 is configured to cause inflation of the at least one inflatable chamber 112. User actuation may thus start the flow of gas from a pressurized gas source 240 coupled to the inflatable chamber(s). The pressurized gas source can be, for example, a carbon dioxide (CO2) canister, a nitrogen cannister, etc. The flow of gas from the pressurized gas source 240 into the inflatable chamber can help stabilize an injury.

The stabilizing structure can be further configured to approximate an anatomical shape upon inflation. Such shapes may include an ankle (FIG. 1), wrist (FIG. 10), shoulder (FIG. 11), hip (FIG. 12), or knee. While the disclosed figures provide exemplary configurations for the apparatus for various types of anatomy, is understood that variations in the structure or design of the disclosed apparatuses are contemplated. For example, general length or size may vary, the number of inflatable chambers may vary, etc. Thus, the depicted examples should not be assumed to limit the claims to the apparatuses particularly depicted. It is also contemplated that the presently disclosed concepts can be applied to apparatuses for treating additional anatomy not specifically depicted herein.

While the illustrated examples depict a stabilizing structure including multiple inflatable chambers, it is contemplated that some implementations may have only a single inflatable chamber. As used herein, when referring to inflatable chambers in the plural, it is contemplated that any features disclosed can apply to a single inflatable chamber.

The cooling structure can be a portion of the apparatus that is able to be cooled in order to apply thermal treatment to a patient. The cooling structure 210 can be, for example, a pouch, sheet, etc., that is in communication with thermally conductive material 230. The single-use cooling element 220 of cooling structure 210 can be configured to cause an endothermic reaction to cause cooling of the cooling structure. In some implementations, the single-use cooling element can include water and ammonium chloride.

An actuator can be configured to cause or initiate mixing of the ammonium chloride and water to generate the endothermic reaction. The apparatus can be further configured to initiate cooling without the need to stir or shake the apparatus. In one such embodiment, cooling may be initiated through effecting removal of a separator located between containers holding water and sodium chloride. For example, cooling may be initiated by removing a separator that covers a significant surface area between the water and sodium chloride containers so that its removal will quickly initiate a substantial endothermic reaction and enable prompt treatment. Removal of the separator may be done, for example, by an actuator configured as a pull tab connected to the separator. This actuator may be the same actuator that initiates inflation of the stabilizing structure, or it may be a second actuator, in addition to the actuator that causes inflation.

It is not necessary for the entirety of the cooling structure to be thermally conductive. Some implementations can include the thermally conductive material 230 on a portion of the cooling structure facing a patient. Such designs may aid in more directly applying cooling to the patient by primarily directing the cooling to such surfaces. In yet other implementations, to further contain the cooling, the cooling structure can include a thermally insulating material between the cooling structure and the stabilizing structure. Examples of thermally insulating materials that can be formed into a layer can include plastic, rubber, foam, cloth, etc.

Figure 3:
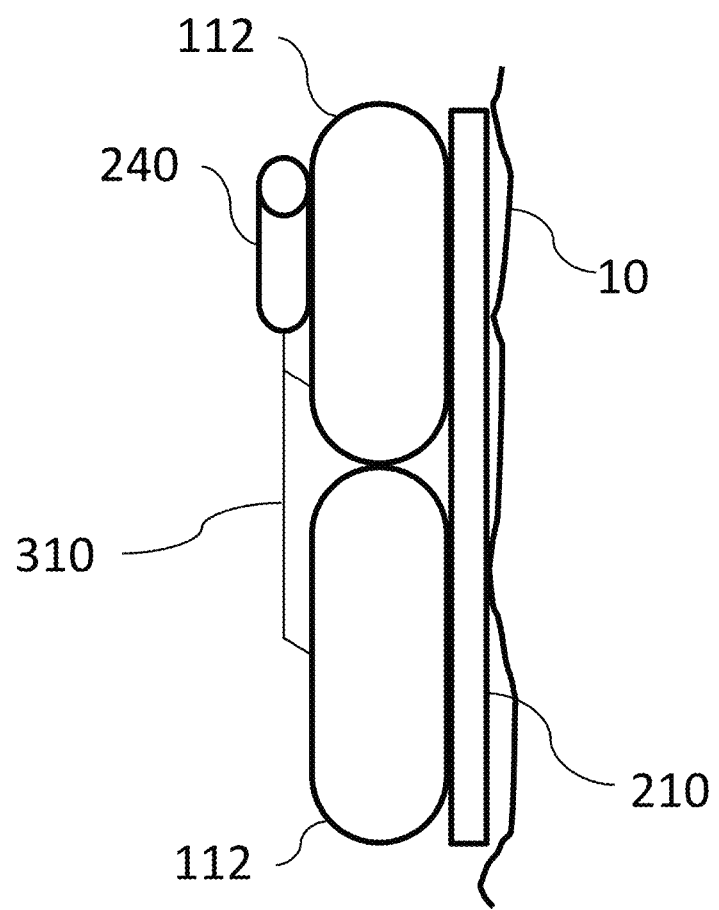
FIG. 3 is a cross-sectional diagram illustrating an exemplary stabilization and cooling apparatus in accordance with certain aspects of the present disclosure.

As shown in FIG. 3, in some implementations, the apparatus can include a manifold 310 connecting the plurality of inflatable chambers 112 to the pressurized gas source. Manifold 310 can be one or more gas lines, such as a hose, tube, or the like, to deliver gas from the pressurized gas source to any or all the inflatable chambers.

The actuator may include an adjustable valve configured for adjustment of pressure in inflatable chamber. For example, such an adjustable valve can be a gas regulator that sets a limit on the inflation pressure of the inflatable chamber. Similarly, to avoid or correct for overpressure, the apparatus can include a pressure relief valve in fluid communication with the inflatable chamber, for example to release excess gas. In implementations where there may be multiple actuators (e.g., pull tabs), one actuator may be configured to allow inflation of one or more inflatable chambers, whereas another actuator may be configured to allow for deflation (in whole or part) of such inflatable chambers. Similarly, one actuator may control inflation/cooling of one group of inflatable chambers and the associated cooling structure, with another actuator controlling a separate group of inflatable chambers/cooling structure.

FIG. 3 depicts an exemplary embodiment where the stabilizing structure and the cooling structure are distinct structures. In one example, the stabilizing structure and cooling structure may be manufactured separately and then affixed to one another (e.g. with an adhesive).

Figure 4:
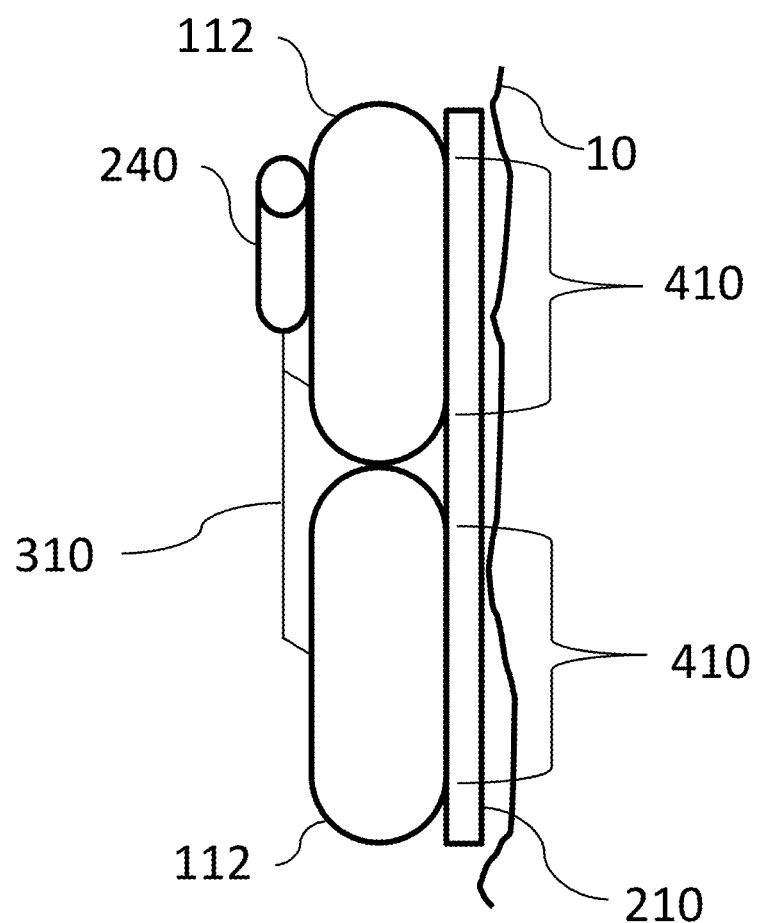
FIG. 4 is a cross-sectional diagram illustrating an exemplary stabilization and cooling apparatus sharing a common wall in accordance with certain aspects of the present disclosure.

FIG. 4 illustrates a similar embodiment to that described in FIG. 3, but instead of the cooling structure and stabilizing structure being distinct components, the cooling structure and the stabilizing structure share a common wall 410. Such implementations may potentially be made of one contiguous piece of material (or largely so), simplifying construction of the apparatus. When sharing a common wall is referred to herein, it is intended to mean sharing all of a particular wall or just a part or parts of the wall.

In certain implementations, to facilitate rapid stabilization and cooling, the actuator that is configured to cause inflation is further configured to also initiate cooling by the cooling element. For example, the actuator can be a single mechanical component, such as a single wire, pull tab, cable, breakable membrane, etc., such that pulling on it causes gas to flow from the pressurized gas source and also causes the cooling element to initiate cooling. In certain implementations, the single mechanical component can be configured to activate the pressured gas source and also break or remove a removable separator to permit reactants in the cooling structure to mix and cool.

Figure 5:
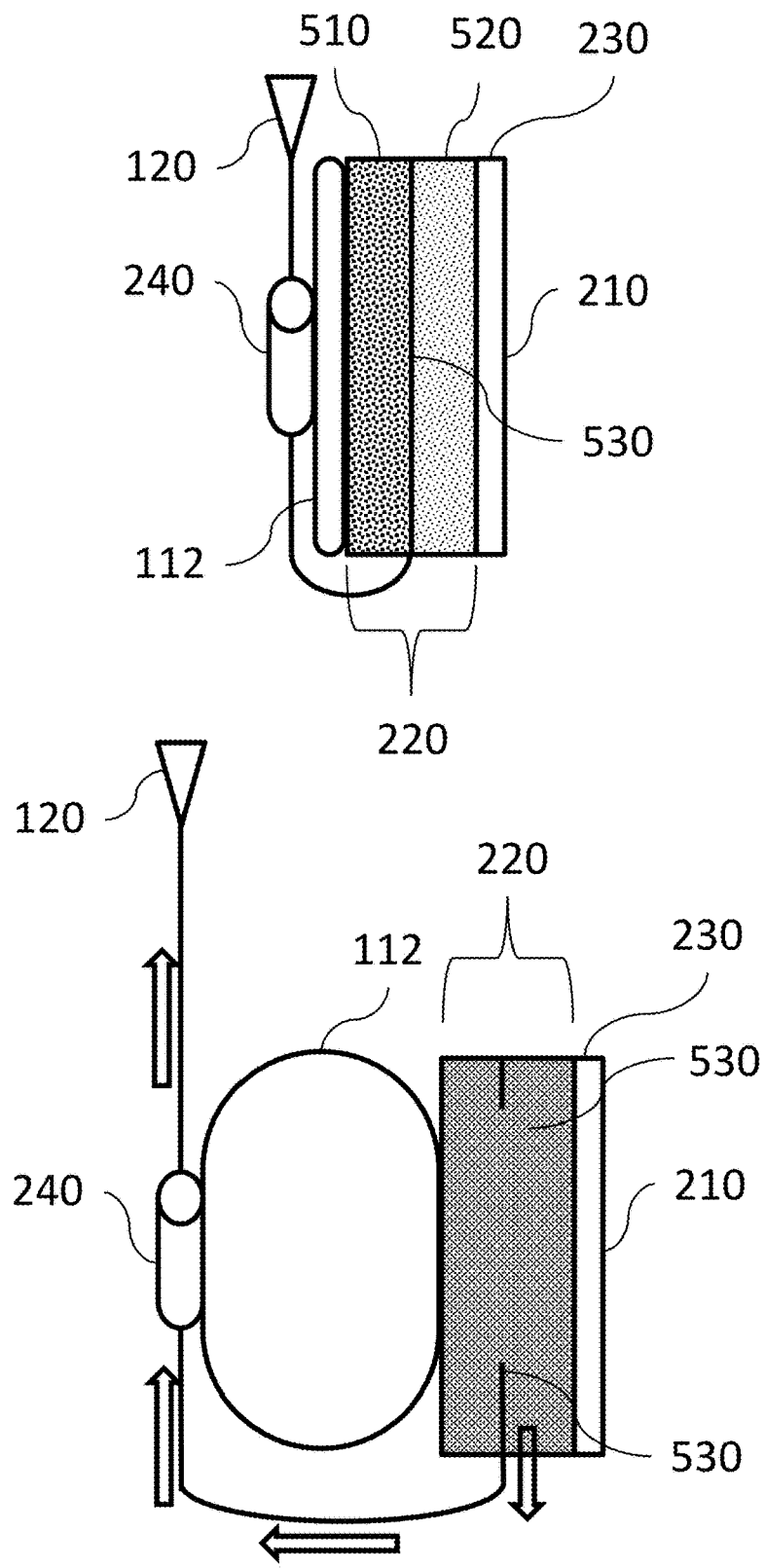
FIG. 5 is a cross-sectional diagram illustrating an exemplary single-actuation mechanism for a stabilization and cooling apparatus in accordance with certain aspects of the present disclosure.

An exemplary depiction of a single actuation embodiment is illustrated in FIG. 5. The top portion of FIG. 5 illustrates a portion of the apparatus prior to actuation. As shown, inflatable chamber 112 is deflated and reactants utilized for cooling are in separated chambers, as described further below. The bottom portion of FIG. 5 depicts the apparatus after actuation, with the inflatable chamber 112 inflated and the reactants mixed to provide cooling.

In some implementations, the cooling element can include a breakable membrane or removable separator 530 separating cooling reactants (e.g., water and ammonium chloride), which when mixed, cause an endothermic reaction. The reactants can be kept separated in reactant chambers (e.g., a first reactant chamber 510 for ammonium chloride and a second reactant chamber 520 for water) until use. As depicted in FIG. 5, the single mechanical component actuator can be pulled and can be configured to activate pressured gas source 240 (e.g., via a switch or valve) and also to break or remove removable separator 530 to permit reactants in the cooling structure to mix and cool. In some implementations, such as depicted in FIG. 5, the breakable membrane or removable separator can have a comparatively large surface area (e.g., all or majority of a side of the reactant chambers). The large surface area allows the then substantially open reactant chambers to quickly mix their respective reactants. The cooled mixture 530 can then can thermally interact with the thermally conductive material 210 to quickly cool the patient.

In other embodiments, inflation of an inflatable chamber can itself cause the initiation of cooling by the cooling element. For example, the mechanical deformation of the inflatable chamber can cause a seal or membrane in the cooling element to break, causing the release of reactants that drive the endothermic cooling reaction.

Figure 5A:
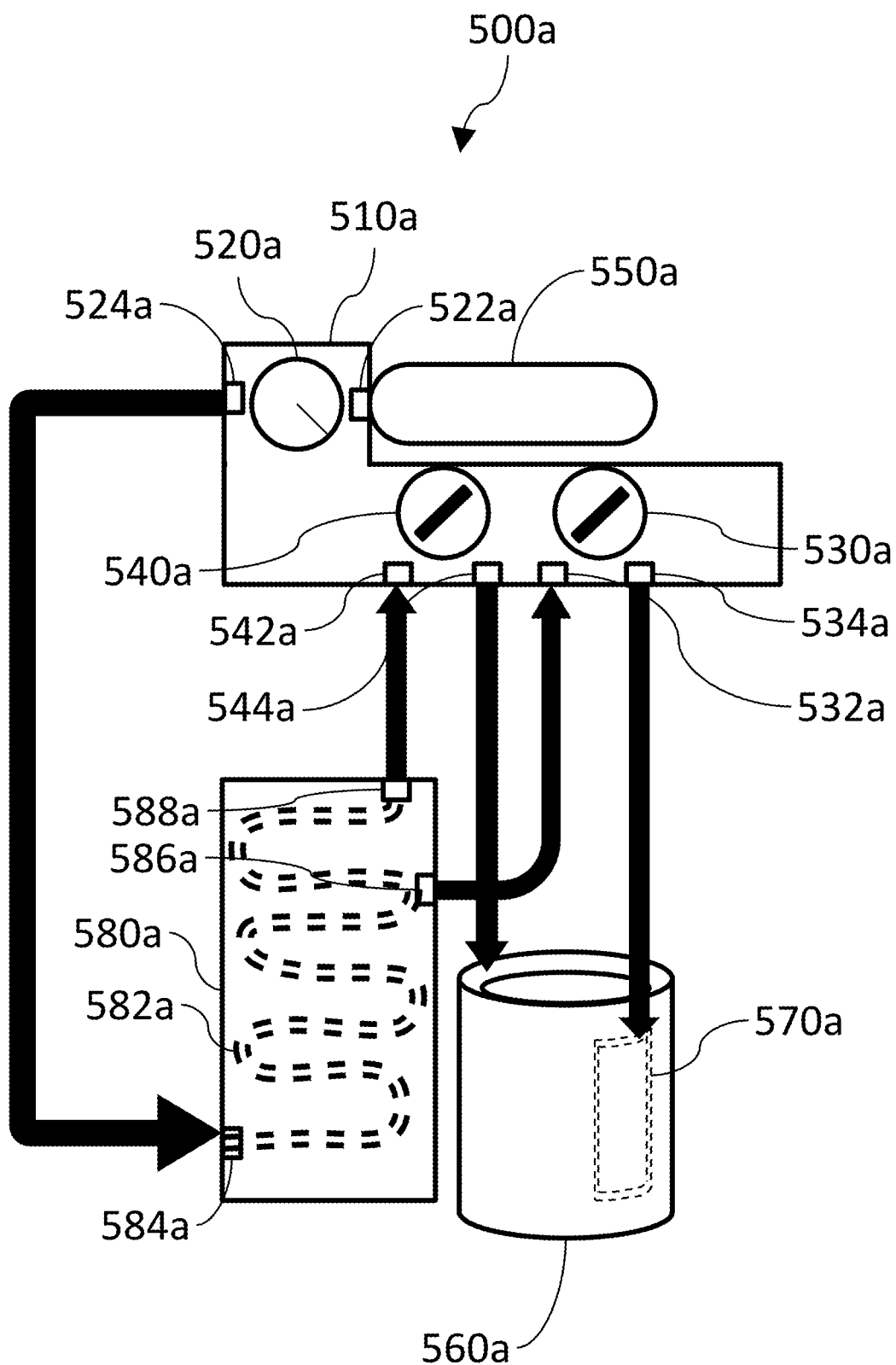
FIG. 5A is a diagram illustrating an exemplary single-actuation mechanism in accordance with certain aspects of the present disclosure.

FIG. 5A is a diagram illustrating an exemplary single-actuation mechanism. As shown in FIG. 5A, an actuator 520*a* can open a pressurized gas source 550*a*. To initiate a cooling reaction, there can be a container 580*a* holding a reactant (e.g., water) and the pressurized gas can cause the reactant to be directed from the container through a first valve 530*a* to a single-use cooling element 570*a*. To initiate inflation (following the reactant being directed to the single-use cooling element), gas from the pressurized gas source can also be directed from the container through a second valve 540*a* and on to inflatable chamber 560*a*. In various embodiments, the inflatable chamber and single-use cooling element can be one of, or similar to, those described in various embodiments throughout the present disclosure.

The single-actuation mechanism 500a can include a housing 510a that can support a gas input port 522a, a gas output port 524a, a first input port 532a, a first output port 534a, a second input port 542a, and a second output port 544a. An actuator 520a can be included and configured to open a pressurized gas source 550a coupled to the gas input port 522a. In addition, the housing 510a can include a first valve 530a configured to direct a reactant from the first input port 532a to the first output port 534a. A second valve 540a can be included and configured to direct gas from the second input port 542a to the second output port 544a. The arrows depicted in FIG. 5A not only show the general direction of fluid flow (gas or liquid) but also represent simplified depictions of lines (e.g., plastic or metal tubing) connecting the various components. Also, the ports described herein can be coupled to any combination of open (i.e., two-way) or check (i.e., one-way) valves. For example, check valves can be utilized to prevent the backflow of reactant and/or gas from a stabilization or cooling apparatus.

The housing can be any structure capable of supporting the components described herein and may be constructed of plastic, metal, etc. The housing can also be integrated with the stabilization and cooling apparatus. However, FIG. 5A shows the housing separate from the inflatable chamber for both clarity of depiction and also because, as described further herein, the housing (and its actuator, valves, etc.) can be considered a separate embodiment, independent of any stabilizing or cooling structure.

In some embodiments, the actuator can be configured to open a pressurized gas source, for example by piercing the top of a pressurized gas source, by unscrewing a cap or plug, breaking a seal, opening a flow valve (which may or may not adjustable), etc. In some embodiments, the actuator can be further configured to adjust a gas pressure from the pressurized gas source. For example, the actuator can cause the pressurized gas source to deliver gas more slowly to provide a desired rate or amount of inflation of the inflatable chamber(s). Similarly, in some embodiments, the actuator can be further configured to close and stop the delivery of gas. Also, in some embodiments, the actuator can be further configured to open and deliver additional gas from the pressurized gas source.

The pressurized gas source can be, for example, a CO2 pressure canister or any other kind of canister, tank, air compressor, etc., that can provide any kind of gas (e.g., air, helium, argon, etc.) at high pressure. The particular pressure utilized can vary as needed, for example, based on the volume of the inflatable chamber(s) that need to be inflated and the desired inflation pressure thereof. The pressurized gas source may also have extra gas to allow additional pressure adjustments by a user. As one nonlimiting example of the pressures contemplated, the pressurized gas source can provide gas at between 20 and 1000 psi. Higher pressures can be utilized to provide the desired rapid cooling and inflation, as well as providing sufficient gas for inflation adjustments. The pressurized gas source can be utilized in combination with any number of step-down regulators (e.g., down to 100 psi) to provide a desired pressure at the container and/or inflatable chamber(s). The pressurized gas source can be welded (or otherwise permanently affixed or integral with) the housing. However, some embodiments can have the pressurized gas source be removable or replaceable.

The exemplary apparatus shown in FIG. 5A includes a container 580a holding a reactant (e.g., water, ammonium chloride, etc.) that can be utilized for initiating cooling in the single-use cooling element. The container can be rigid (e.g., made of hard rubber, plastic, metal, etc.) or flexible (e.g., made of soft rubber, thin plastic, etc.). In some embodiments, the container can include one or more internal cavities 582a for holding the reactant. In some embodiments, the internal cavity can be elongated to provide a generally directed flow of gas or reactant through the internal cavity. To reduce the physical footprint of the container, some embodiments of the internal cavity can formed in a serpentine manner (as shown by the example in FIG. 5A), wound into a spiral, folded, etc. Embodiments of the container can include ports for the delivery of reactant and/or gas. As shown in the example of FIG. 5A, the container can include a third gas input port 584a (to receive gas from the pressurized gas source), a third output port 586a (to provide reactant to the first input port), and a third output port 588a (to provide gas to the second input port). The various ports described can be at any location on the container. For an exemplary elongated internal cavity, the third input port can be at one end of the internal cavity, and the third output port can be at the other end of the internal cavity, with the third output port disposed anywhere between the third input port and the third output port. Other designs are contemplated, for example, the third output port could be connected to the line between the container and the second valve.

Opening the pressurized gas source 550a can cause the reactant to be directed from the container 580a to the single-use cooling element 570a through the first valve 530a. In some implementations, the first valve (and second valve, or any valves disclosed herein) can be pressure-adjustable, e.g., being a diaphragm-pressure adjustable valve, and thereby can be configured to open at a first threshold pressure. Having a threshold opening pressure can prevent reactant from the container from prematurely entering the single-use cooling element. In some embodiments, the amount of reactant in the container can be approximately equal to the amount of reactant that the single-use cooling element can contain. For example, the single-use cooling element can include pellets (e.g., urea pellets that endothermically react with water) of generally small volume compared to that of the reactant. As used herein, "approximately equal" means that when the single-use cooling element is full (e.g., having most or all of the reactant) the container is sufficiently depleted of reactant to be able to convey sufficient gas pressure to the second valve to cause it to open, as described further herein. In other embodiments, the single-use cooling element may only be partially full (having as much reactant as was in the container) or may be full but some reactant remaining in the lines, and even possibly in the container.

Gas from the pressurized gas source 550a can also cause inflation of the inflatable chamber 560a through the second valve 540a. The inflation can occur following the reactant being directed to the single-use cooling element through the first valve 530a. As used herein, inflation "following" direction of the reactant to the single-use cooling element can occur any time after gas from the pressurized gas source enters the container. However, as described below for various embodiments, there may be a delay while the gas pressure builds up enough to open the second valve. After gas has moved some or all of the reactant to the single-use cooling element, the pressure in the container can continue to increase. The second valve 540a (in communication with the container 580a) may be configured to open at a second threshold pressure that is higher than the first threshold pressure. In some embodiments, the second valve opening may cause closing of the first valve (e.g., by the valves being mechanically interconnected), thereby preventing backflow of reactant into the container and/or inflatable chamber. The inflatable chamber 560a can then inflate to the desired pressure utilizing the gas from the pressurized gas source 550a. In some embodiments, a relief valve may be provided anywhere in the system (e.g., along any gas line or otherwise in communication with the inflatable chamber) to allow gas to escape in order to reduce the inflation pressure.

While the present disclosure contemplates that the above single-actuation mechanisms may be utilized with any of the stabilization and cooling devices provided herein, any of the disclosed single-actuation mechanisms can be utilized with other types of apparatuses to provide various technical benefits, for example, any apparatus that would benefit from a two-stage delivery of gas and/or liquid. Accordingly, it is not essential that the disclosed single actuation mechanisms particularly require stabilization structures or cooling structures.

Figure 6:
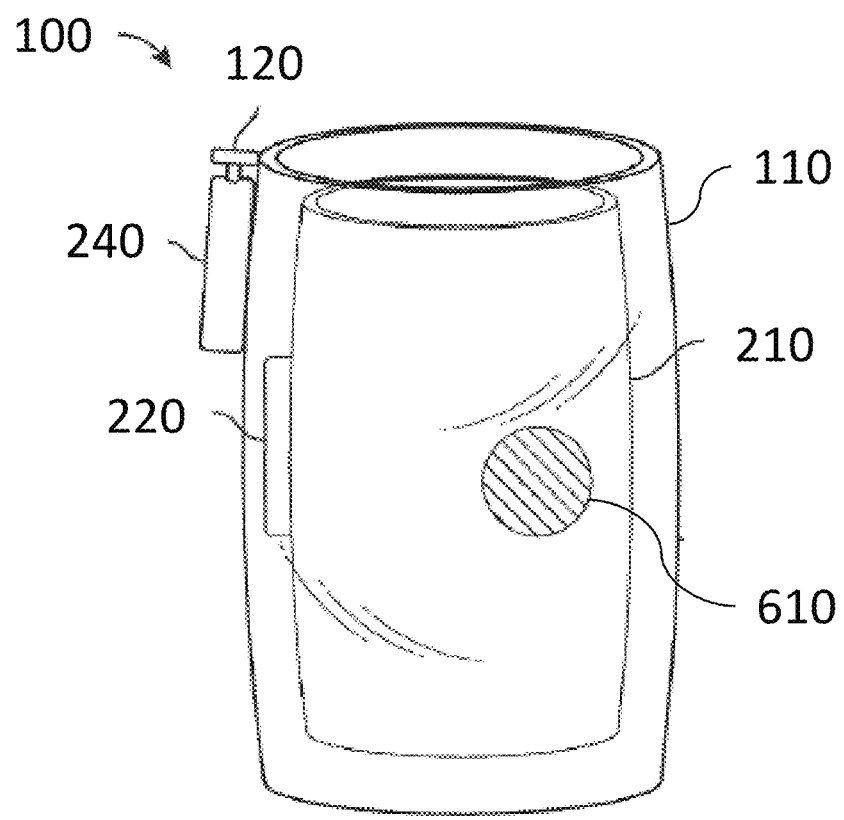
FIG. 6 is a simplified diagram illustrating an exemplary alignment hole included with a stabilization and cooling apparatus in accordance with certain aspects of the present disclosure.

FIG. 6 illustrates an embodiment where the stabilizing structure and/or the cooling structure can include an alignment hole 610 that facilitates alignment of the apparatus 100 on patient anatomy. The alignment hole can extend through at least a portion of the apparatus (e.g., partially, to provide a general orientation for the apparatus relative to the patient, or wholly, to allow unobstructed access to the patient). The alignment hole can be approximately sized and shaped for an elbow, kneecap, anklebone, shoulder joint, or other portion of the patient's anatomy. In this way, application of the apparatus can be improved by ensuring that it is properly located prior to inflation. The disposition of the alignment hole can further ensure that when the apparatus is inflated to form a semirigid structure, that the patient's anatomy is immobilized in the proper configuration.

Figure 7:
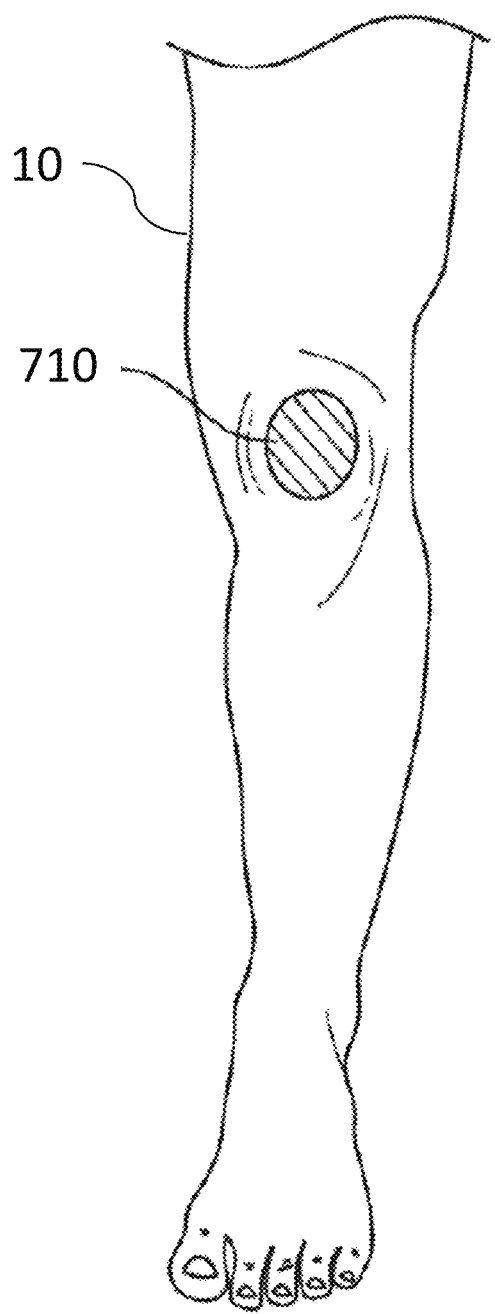
FIGS. 7-8 are simplified diagrams illustrating an exemplary use of the stabilization and cooling apparatus in accordance with certain aspects of the present disclosure.
Figure 8:
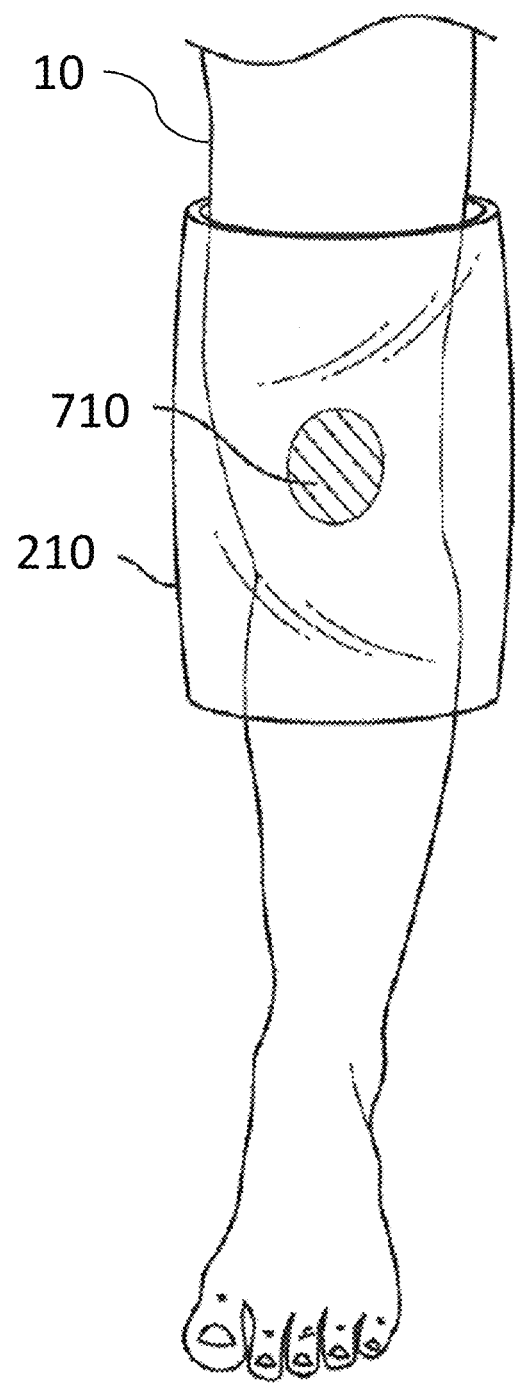

With certain embodiments of the present disclosure having been discussed, an example of use is provided of an apparatus configured to immobilize and cool an injury to a patient's knee. FIG. 7 depicts the leg of a patient with an injury site 710 shown at the knee. As shown in FIG. 8, one method of injury stabilization and cooling can include applying, to an injured portion of a patient, an apparatus in accordance with any of the disclosed embodiments, in this example, an apparatus for the knee. The method can also include activating the actuator to cause inflation of the inflatable chambers in order to stabilize the injured portion and also to cause cooling in order to cool the injured portion.

Figure 9:
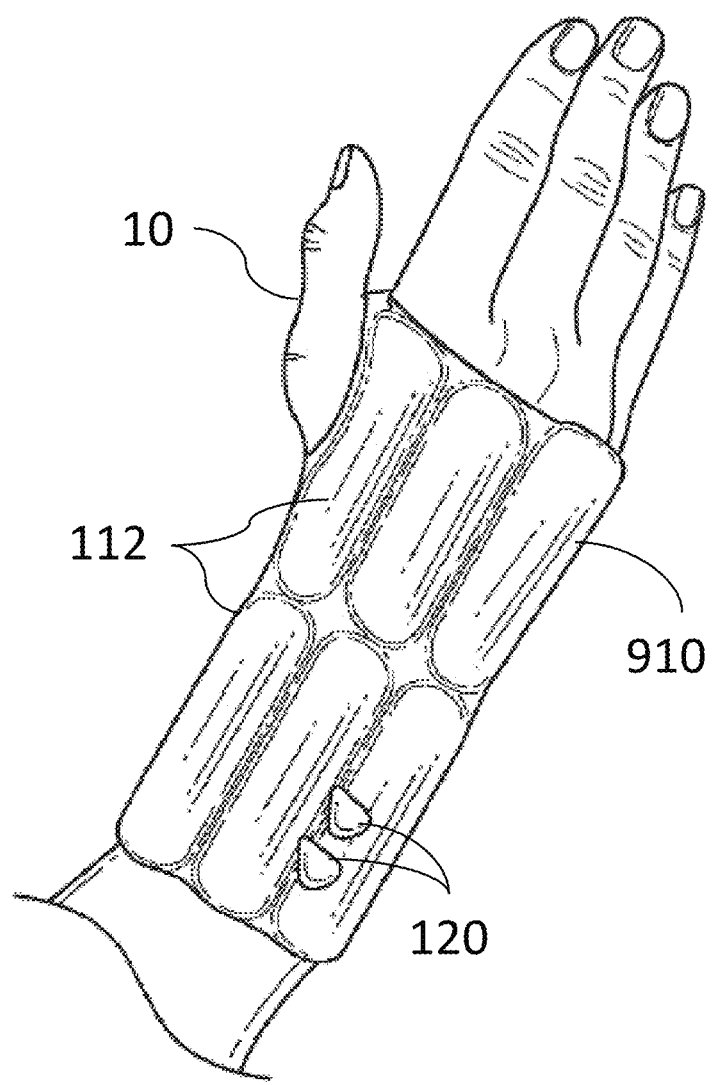
FIG. 9 is a simplified diagram illustrating an exemplary stabilization and cooling apparatus configured to be worn on the wrist in accordance with certain aspects of the present disclosure.

FIG. 9 depicts an implementation of an exemplary apparatus 910 configured to immobilize and cool a wrist. Similar to other embodiments disclosed herein, apparatus 910 includes numerous inflation chambers and actuators to enable stabilization and cooling of a wrist. The apparatus 910 also includes a hole to allow the patient's thumb to emerge from a side of the apparatus.

Figure 10:
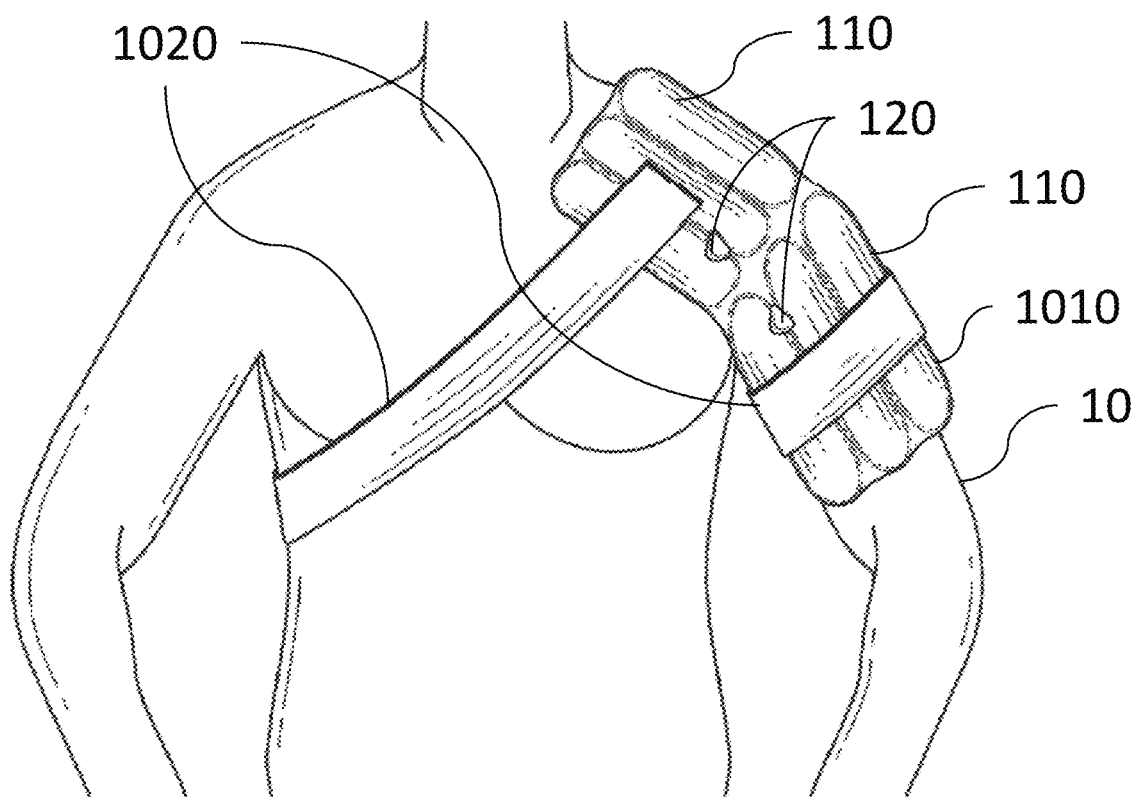
FIG. 10 is a simplified diagram illustrating an exemplary stabilization and cooling apparatus configured to be worn on the shoulder in accordance with certain aspects of the present disclosure.

FIG. 10 depicts an exemplary implementation of an apparatus configured to immobilize and cool a shoulder. Similar to other embodiments disclosed herein, apparatus 1010 includes numerous inflation chambers and actuators to enable stabilization and cooling of a shoulder. Such implementations can include one or more securing straps 1020 attached to the stabilizing structure 110 and configured to facilitate securing the apparatus to patient 10. The securing straps can be cloth, plastic, elastic, etc. and can be tightened via buckles, snaps, etc.

Figure 11:
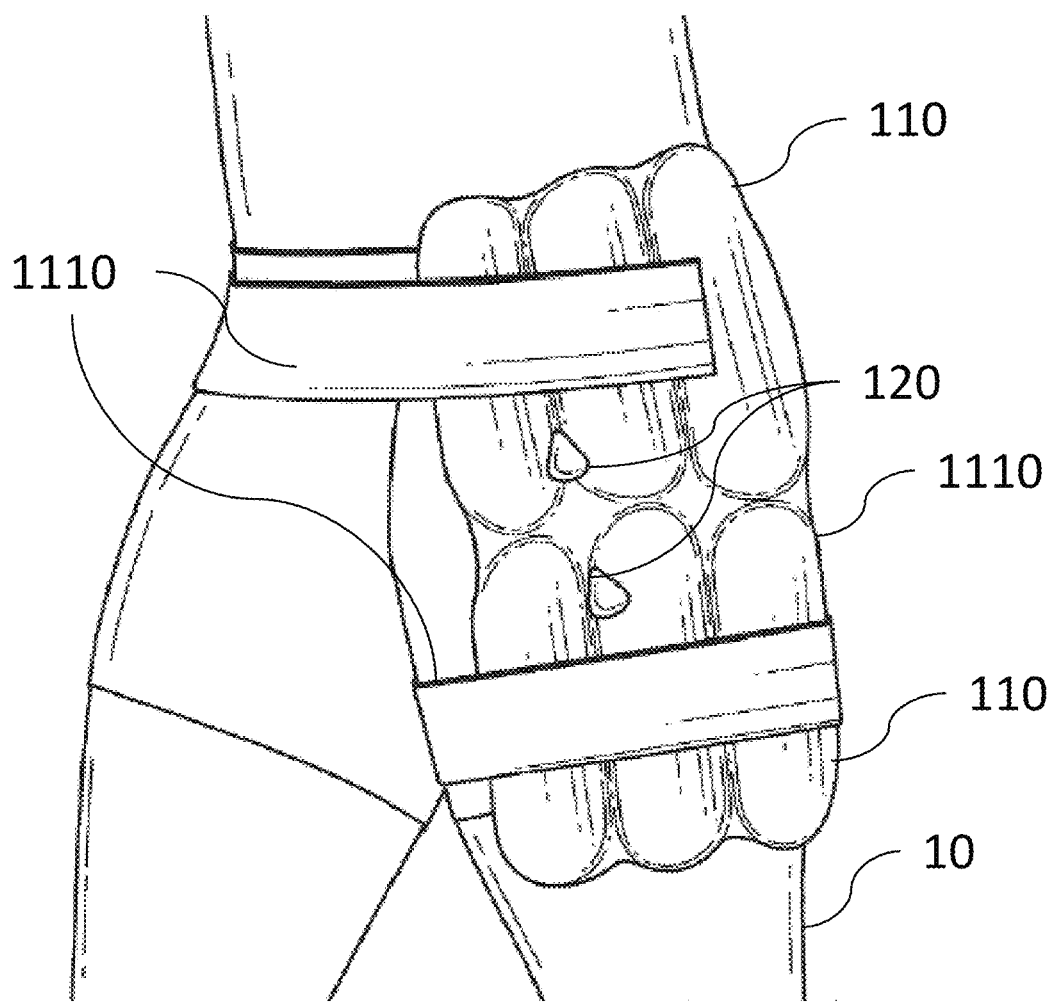
FIG. 11 is an exemplary simplified diagram illustrating a stabilization and cooling apparatus configured to be worn on the hip or thigh in accordance with certain aspects of the present disclosure.

FIG. 11 depicts an exemplary implementation of an apparatus configured to immobilize and cool a hip or thigh. Similar to other embodiments disclosed herein, apparatus 1110 includes numerous inflation chambers and actuators to enable stabilization and cooling of the hip or thigh. Such implementations can also include one or more securing straps similar to those discussed with reference to the shoulder apparatus of FIG. 10.

In the following, further features, characteristics, and exemplary technical solutions of the present disclosure will be described in terms of items that may be optionally claimed in any combination:

Item 1: A stabilization and cooling apparatus comprising: a stabilizing structure including at least one inflatable chamber, the stabilizing structure configured to become semi-rigid upon inflation of the at least one inflatable chamber; a cooling structure integrated with the stabilizing structure including a single-use cooling element and a thermally conductive material in thermal communication with the single-use cooling element; and an actuator configured to cause inflation of the at least one inflatable chamber.

Item 2: the apparatus of any of the preceding items, wherein the stabilizing structure is further configured to approximate an anatomical shape upon inflation.

Item 3: the apparatus of any of the preceding items, wherein the anatomical shape is a wrist, shoulder, hip, knee, or ankle.

Item 4: the apparatus of any of the preceding items, the stabilizing structure further comprising a pressurized gas source coupled to the at least one inflatable chamber.

Item 5: the apparatus of any of the preceding items, wherein the pressurized gas source is a CO2 canister.

Item 6: the apparatus of any of the preceding items, wherein the stabilizing structure includes a plurality of inflatable chambers.

Item 7: the apparatus of any of the preceding items, further comprising a manifold connecting the plurality of inflatable chambers to the pressurized gas source.

Item 8: the apparatus of any of the preceding items, wherein the actuator is a pull tab.

Item 9: the apparatus of any of the preceding items, wherein the actuator includes an adjustable valve configured for adjustment of pressure in the at least one inflatable chamber.

Item 10: the apparatus of any of the preceding items, further comprising a pressure relief valve in fluid communication with the at least one inflatable chamber.

Item 11: the apparatus of any of the preceding items, wherein the stabilizing structure includes an alignment hole that facilitates alignment of the apparatus on patient anatomy.

Item 12: the apparatus of any of the preceding items, further comprising one or more securing straps attached to the stabilizing structure and configured to facilitate securing the apparatus to a patient.

Item 13: the apparatus of any of the preceding items, wherein the single-use cooling element is configured to cause an endothermic reaction.

Item 14: the apparatus of any of the preceding items, wherein the single-use cooling element includes water and ammonium chloride.

Item 15: the apparatus of any of the preceding items, further comprising a second actuator, wherein the second actuator is configured to cause mixing of the ammonium chloride and water to generate the endothermic reaction.

Item 16: the apparatus of any of the preceding items, wherein the apparatus is further configured to initiate cooling without the need to stir or shake the apparatus.

Item 17: the apparatus of any of the preceding items, wherein the apparatus is further configured to initiate cooling through removal of a separator located between containers holding water and sodium chloride.

Item 18: the apparatus of any of the preceding items, wherein the cooling structure is disposed inside the stabilizing structure.

Item 19: the apparatus of any of the preceding items, wherein the thermally conductive material is on a portion of the cooling structure facing a patient and the cooling structure further includes a thermally insulating material between the cooling structure and the stabilizing structure.

Item 20: the apparatus of any of the preceding items, wherein the cooling structure and the stabilizing structure share a common wall.

Item 21: the apparatus of any of the preceding items, wherein the actuator is further configured to also initiate cooling by the single-use cooling element.

Item 22: the apparatus of any of the preceding items, wherein the actuator is a single mechanical component.

Item 23: the apparatus of any of the preceding items, wherein the single mechanical component can be configured to activate a pressured gas source and also break or remove a removable separator to permit reactants in the cooling structure to mix and cool.

Item 24: the apparatus of any of the preceding items, wherein inflation of the at least one inflatable chamber causes the initiation of cooling by the single-use cooling element.

Item 25: the apparatus of any of the preceding items, wherein the actuator is further configured to open a pressurized gas source.

Item 26: the apparatus of any of the preceding items, wherein the actuator is configured to open the pressurized gas source by piercing of the pressurized gas source.

Item 27: the apparatus of any of the preceding items, further comprising a container holding a reactant, and wherein opening the pressurized gas source causes the reactant to be directed from the container to the single-use cooling element through a first valve.

Item 28: the apparatus of any of the preceding items, wherein gas from the pressurized gas source causes inflation of the at least one inflatable chamber through a second valve, following the reactant being directed to the single-use cooling element through the first valve.

Item 29: the apparatus of any of the preceding items, wherein the first valve is configured to open at a first threshold pressure.

Item 30: the apparatus of any of the preceding items, wherein the second valve is configured to open at a second threshold pressure that is higher than the first threshold pressure.

Item 31: the apparatus of any of the preceding items, wherein the actuator is further configured to adjust a gas pressure from the pressurized gas source.

Item 32: the apparatus of any of the preceding items, wherein the actuator is further configured to close and stop the delivery of gas.

Item 33: the apparatus of any of the preceding items, wherein the actuator is further configured to open and deliver additional gas.

Item 34: an apparatus comprising: a housing comprising a gas input port, a gas output port, a first input port, a first output port, a second input port, and a second output port; an actuator configured to open a pressurized gas source coupled to the gas input port; a first valve configured to direct a reactant from the first input port to the first output port; and a second valve configured to direct gas from the second input port to the second output port.

Item 35: the apparatus of any of the preceding items, further comprising a container holding the reactant, and wherein opening the pressurized gas source causes the reactant to be directed from the container to a single-use cooling element through the first valve.

Item 36: the apparatus of any of the preceding items, wherein gas from the pressurized gas source causes inflation of at least one inflatable chamber through the second valve, following the reactant being directed to the single-use cooling element through the first valve.

Item 37: the apparatus of any of the preceding items, wherein the first valve is configured to open at a first threshold pressure.

Item 38: the apparatus of any of the preceding items, wherein the second valve is configured to open at a second threshold pressure that is higher than the first threshold pressure.

Item 39: the apparatus of any of the preceding items, further comprising a container, wherein first valve directs the reactant from the container to the single-use cooling element.

Item 40: the apparatus of any of the preceding items, wherein the actuator is further configured to adjust a gas pressure from the pressurized gas source.

Item 41: the apparatus of any of the preceding items, wherein the actuator is further configured to close and stop the delivery of gas.

Item 42: the apparatus of any of the preceding items, wherein the actuator is further configured to open and deliver additional gas.

Item 43: A method comprising: applying, to an injured portion of a patient, an apparatus in accordance with any of the previous items; and activating the actuator to cause inflation of the at least one inflatable chamber in order to stabilize the injured portion and also to cause cooling in order to cool the injured portion.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A stabilization and cooling apparatus comprising: a stabilizing structure including at least one inflatable chamber, the stabilizing structure configured to become semi-rigid upon inflation of the at least one inflatable chamber, wherein the stabilizing structure is semi-rigid to prevent movement of an injured joint of a patient; a cooling structure integrated with the stabilizing structure including a single-use cooling element and a thermally conductive material in thermal communication with the single-use cooling element; a container holding a reactant; and an actuator configured to cause the inflation of the at least one inflatable chamber, to initiate cooling by the single-use cooling element, and to open a pressurized gas source; wherein opening the pressurized gas source causes the reactant to be directed from the container to the single-use cooling element through a first valve; wherein gas from the pressurized gas source causes the inflation of the at least one inflatable chamber through a second valve, following the reactant being directed to the single-use cooling element through the first valve.

2. The stabilization and cooling apparatus of claim 1, wherein the first valve is configured to open at a first threshold pressure.

3. The stabilization and cooling apparatus of claim 2, wherein the second valve is configured to open at a second threshold pressure that is higher than the first threshold pressure.

4. The stabilization and cooling apparatus of claim 1, wherein the actuator is configured to open the pressurized gas source by piercing of the pressurized gas source.

5. The stabilization and cooling apparatus of claim 1, wherein the actuator is further configured to adjust a gas pressure from the pressurized gas source.

6. The stabilization and cooling apparatus of claim 1, wherein the actuator is further configured to close and stop delivery of gas.

7. The stabilization and cooling apparatus of claim 1, wherein the actuator is further configured to open and deliver additional gas.

8. A method comprising:
applying, to an injured portion of a patient, the apparatus of claim 1; and
activating the actuator to cause inflation of the at least one inflatable chamber in order to stabilize the injured portion and also to cause cooling in order to cool the injured portion.

9. An apparatus comprising:
a housing comprising a gas input port, a gas output port, a first input port, a first output port, a second input port, and a second output port;
an actuator configured to open a pressurized gas source coupled to the gas input port;
a first valve configured to direct a reactant from the first input port to the first output port;
a second valve configured to direct gas from the second input port to the second output port; and
a container holding the reactant, wherein opening the pressurized gas source causes the reactant to be directed from the container to a single-use cooling element through the first valve;
wherein gas from the pressurized gas source causes inflation of at least one inflatable chamber through the second valve, following the reactant being directed to the single-use cooling element through the first valve.

10. The apparatus of claim 9, wherein the first valve is configured to open at a first threshold pressure.

11. The apparatus of claim 10, wherein the second valve is configured to open at a second threshold pressure that is higher than the first threshold pressure.

12. The apparatus of claim 9, wherein the first valve directs the reactant from the container to the single-use cooling element.

13. The apparatus of claim 9, wherein the actuator is further configured to adjust a gas pressure from the pressurized gas source.

14. The apparatus of claim 9, wherein the actuator is further configured to close and stop delivery of gas.

15. The apparatus of claim 9, wherein the actuator is further configured to open and deliver additional gas.

* * * * *